US010160644B1

(12) United States Patent
Kinoshita et al.

(10) Patent No.: US 10,160,644 B1
(45) Date of Patent: Dec. 25, 2018

(54) MANUFACTURING METHOD OF MEMS SENSOR

(71) Applicant: Hitachi, Ltd., Chiyoda-ku, Tokyo (JP)

(72) Inventors: Masaharu Kinoshita, Tokyo (JP); Atsushi Isobe, Tokyo (JP); Kazuo Ono, Tokyo (JP); Noriyuki Sakuma, Tokyo (JP); Tomonori Sekiguchi, Tokyo (JP); Keiji Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/918,502

(22) Filed: Mar. 12, 2018

(30) Foreign Application Priority Data

Jun. 26, 2017 (JP) .................................. 2017-123905

(51) Int. Cl.
*B81C 1/00* (2006.01)
*B81B 3/00* (2006.01)
*G01N 29/24* (2006.01)
*B06B 1/02* (2006.01)

(52) U.S. Cl.
CPC ........ *B81C 1/00817* (2013.01); *B06B 1/0292* (2013.01); *B81B 3/0021* (2013.01); *B81C 1/00047* (2013.01); *B81C 1/00293* (2013.01); *G01N 29/2406* (2013.01); *B81B 2201/0271* (2013.01); *B81B 2203/0315* (2013.01); *B81C 2201/0143* (2013.01); *B81C 2203/0145* (2013.01)

(58) Field of Classification Search
CPC .......... B81B 2203/0315; B06B 1/0292; B81C 1/00047; B81C 1/00817
See application file for complete search history.

(56) References Cited

U.S. PATENT DOCUMENTS

| 5,982,709 A | * | 11/1999 | Ladabaum | .......... | H01L 41/0973 |
| | | | | | 367/170 |
| 7,830,069 B2 | * | 11/2010 | Lukacs | ................. | B06B 1/0622 |
| | | | | | 310/334 |
| 9,067,779 B1 | * | 6/2015 | Rothberg | ............ | B81C 1/00238 |

FOREIGN PATENT DOCUMENTS

JP          2009-4591 A      1/2009

* cited by examiner

*Primary Examiner* — Joseph C Nicely
*Assistant Examiner* — Wilner Jean Baptiste
(74) *Attorney, Agent, or Firm* — Crowell & Moring LLP

(57) ABSTRACT

A manufacturing method of a MEMS sensor includes a step of, by irradiating a first hole formed in a second layer on a semiconductor substrate with a focused ion beam for a first predetermined time, forming a first sealing film, which seals the first hole, on the first hole, and a step of, by irradiating a second hole formed in the second layer with a focused ion beam for a second predetermined time, forming a second sealing film, which seals the second hole, on the second hole. At this time, each of the first predetermined time and the second predetermined time is a time in which thermal equilibrium of the second layer is maintainable, and the step of forming the first sealing film and the step of forming the second sealing film are performed repeatedly.

15 Claims, 11 Drawing Sheets

MANUFACTURING METHOD OF MEMS SENSOR

CROSS-REFERENCE TO RELATED APPLICATION

The present application claims priority from Japanese Patent Application No. 2017-123905 filed on Jun. 26, 2017, the content of which is hereby incorporated by reference into this application.

TECHNICAL FIELD OF THE INVENTION

The present invention relates to a manufacturing method of a MEMS sensor.

BACKGROUND OF THE INVENTION

For manufacture of a MEMS (Micro Electro Mechanical System) sensor, a sensor manufacturing process through direct modeling by use of a focused ion beam (FIB) has been studied to achieve a manufacturing process with a shorter TAT (turn-around time). Manufacturing a MEMS sensor having a cavity, in particular, requires a process of sealing/protecting an element of the sensor for the purpose of making the cavity vacuum to improve the performance of the sensor.

Japanese Patent Application Laid-Open Publication No. 2009-4591 (Patent Document 1) discloses a technique in which a micro-sampling piece is extracted and a corresponding sampling hole formed in a semiconductor wafer is repaired by use of a focused ion beam.

SUMMARY OF THE INVENTION

In a MEMS sensor such as an ultrasonic sensor, when a cavity formed between an upper electrode and a lower electrode is sealed by a focused ion beam, the number of sealing spots is large (a total sealing volume is large), thereby causing a longer manufacturing time.

Meanwhile, in order to eliminate the above problem of the longer manufacturing time, a deposition rate by the focused ion beam is increased, whereby another problem that the MEMS sensor is destroyed by heat is caused.

Note that the above patent document (Japanese Patent Application Laid-Open Publication No. 2009-4591) does not describe structural destruction by heat, and describes only the method of filling up a single hole without describing a method of efficiently filling up a plurality of holes.

An object of the present invention is to provide a technique in which, in manufacture of a MEMS sensor, a TAT can be shortened and thermal destruction of the MEMS sensor can be prevented.

Other objects and novel characteristics of the present invention will be apparent from the description of the present specification and the accompanying drawings.

The typical ones of the embodiments disclosed in the present application will be briefly described as follows.

A manufacturing method of a MEMS sensor according to one embodiment, the method includes the steps of:

(a) preparing a substrate on which a first layer and a second layer on the first layer via a cavity are formed and including a first hole and a second hole that are formed in the second layer in such a way as to communicate with the cavity;

(b) after the step (a), by irradiating the first hole with a focused ion beam for a first predetermined time, forming a first sealing film that seals the first hole on the first hole; and (c) after the step (b), by irradiating the second hole with a focused ion beam for a second predetermined time, forming a second sealing film that seals the second hole on the second hole. In this method, each of the first predetermined time and the second predetermined time is a time in which thermal equilibrium of the second layer is maintainable, and the step (b) and the step (c) are performed repeatedly.

A manufacturing method of a MEMS sensor according to another embodiment, the method includes the step of:

on a substrate, forming a first layer and a second layer on the first layer via a cavity, and by irradiating each of a plurality of holes formed in the second layer in such a way as to communicate with the cavity with a focused ion beam having a predetermined beam current density, forming a plurality of sealing films each sealing each of the plurality of holes, on the plurality of holes, respectively. Further, the predetermined beam current density is a beam current density at which thermal equilibrium of the second layer is maintainable, and the plurality of sealing films are formed simultaneously.

Also, a manufacturing method of a MEMS sensor according to another embodiment, the method includes the steps of:

(a) on a substrate, forming a first layer, a second layer on the first layer, and a third layer between the first layer and the second layer;

(b) after the step (a), by irradiating a first hole formation spot of the second layer with a focused ion beam for a first predetermined time, forming a first hole in the second layer such that the first hole reaches the third layer;

(c) after the step (b), by irradiating a second hole formation spot of the second layer with a focused ion beam for a second predetermined time, forming a second hole in the second layer such that the second hole reaches the third layer;

(d) after the step (c), removing the third layer through the first hole and the second hole and then forming a cavity between the first layer and the second layer in such a way as to communicate with the first hole and the second hole; and (e) after the step (d), forming a sealing film on each of the first hole and the second hole. Each of the first predetermined time and the second predetermined time is a time in which thermal equilibrium of the second layer is maintainable, and before the step (d), the step (b) and the step (c) are performed repeatedly.

Effects obtained by the typical ones of the inventions disclosed in the present application will be briefly described as follows.

In manufacture of a MEMS sensor, the TAT can be shortened, and thermal destruction of the MEMS sensor can be prevented.

BRIEF DESCRIPTIONS OF THE DRAWINGS

DESCRIPTIONS OF THE PREFERRED EMBODIMENTS

First Embodiment

A structure of an ultrasonic sensor, which is one embodiment of a MEMS sensor of the present invention, will be described with reference to the drawings.

<Structure of Ultrasonic Sensor>

Figure 1:
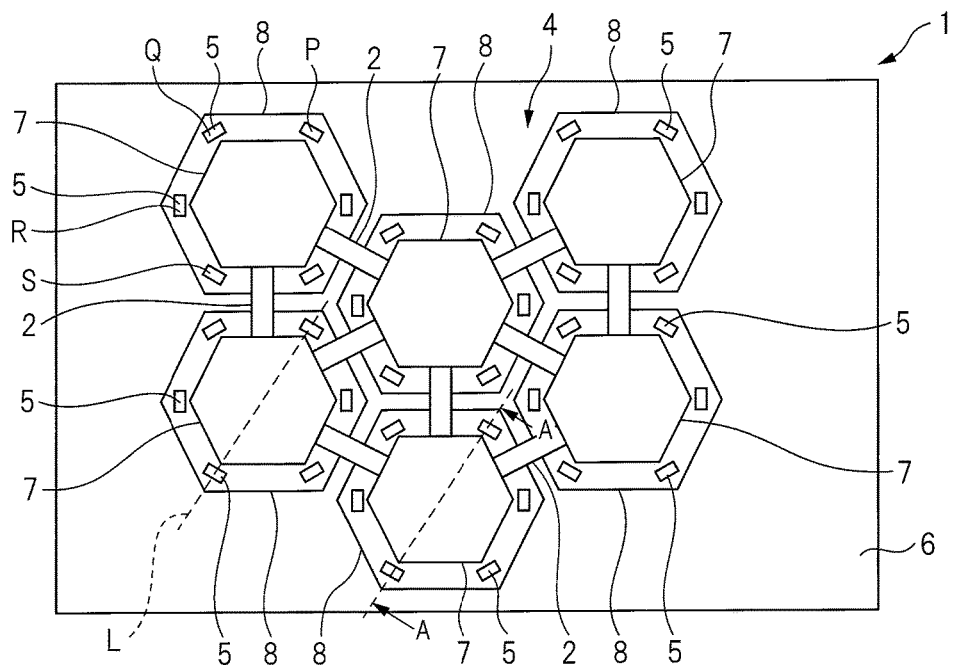
FIG. 1 is a plan view of a principle portion of a MEMS sensor according to a first embodiment of the present invention.
Figure 2:
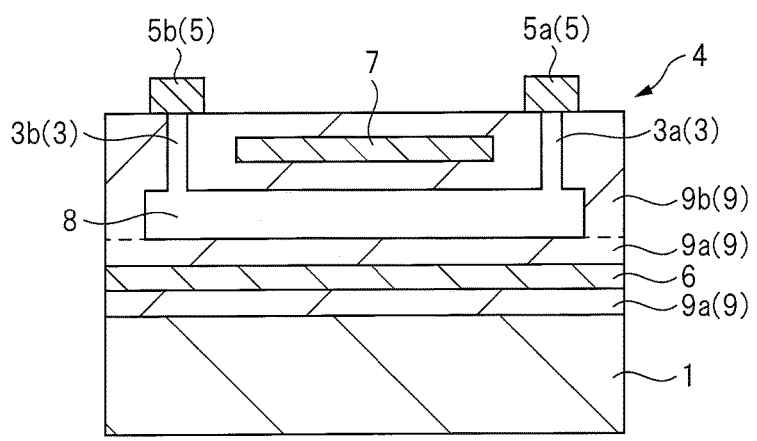
FIG. 2 is a cross-sectional view of a structure taken along a line A-A of FIG. 1.

FIG. 1 is a plan view of a principle portion of a MEMS sensor according to a first embodiment of the present invention. FIG. 2 is a cross-sectional view of a structure taken along a line A-A of FIG. 1.

An ultrasonic sensor (MEMS sensor) 4 according to the first embodiment is a capacitive micro-machined ultrasonic transducer (CMUT) to which a semiconductor technique is applied.

The ultrasonic sensor 4 of the first embodiment shown in FIGS. 1 and 2 is manufactured on a substrate such as a semiconductor substrate 1 by patterning a plurality of micro sensors by lithography. Each micro sensor is structured such that a cavity 8 having a vacuum atmosphere is formed in an insulating layer, with electrodes being formed below and above the cavity 8.

An electrostatic force is applied between these electrodes to cause an electrode film to vibrate, thereby transmitting an ultrasonic signal. Upon receiving a signal, the micro sensor converts a displacement amount of the electrode film into a change in capacitance to detect a signal.

More specifically, in the structure of the ultrasonic sensor 4 of the first embodiment shown in FIGS. 1 and 2, a plurality of micro sensors (ultrasonic sensors 4, which are also called cells) each made into hexagon in a plan view are disposed in the insulating layer on the semiconductor substrate 1 to spread across the insulating layer.

In the first embodiment, description will be given of a case in which each ultrasonic sensor 4 has a silicon oxide film ($SiO_2$ film) 9 which is the insulating layer formed on the semiconductor substrate 1 and composed of a first layer and a second layer. Specifically, a silicon oxide film ($SiO_2$ film) 9a serving as the first layer is formed on the semiconductor substrate 1, and a silicon oxide film ($SiO_2$ film) 9b serving as the second layer is formed on the silicon oxide film 9a via the cavity 8. Further, in the silicon oxide film 9a, a lower electrode (first electrode) 6 is formed. Meanwhile, in the silicon oxide film 9b, an upper electrode (second electrode) 7 having a hexagonal shape in a plan view is formed.

That is, the ultrasonic sensor 4 includes a plurality of the lower electrodes 6 and a plurality of the upper electrodes 7 that are disposed opposite to each other with a plurality of the cavities 8 interposed therebetween in a film thickness direction.

Note that, as shown in FIG. 1, each pair of upper electrodes 7 adjacent to each other are electrically connected through a wiring 2, so that one upper electrode 7 and another upper electrode 7 distant therefrom are also electrically connected through any of the wirings 2.

In addition, as shown in FIG. 2, the cavity 8 formed between the lower electrode 6 and the upper electrode 7 has a plurality of holes 3 formed therein in such a way as to communicate with the cavity 8. For example, in the silicon oxide film 9b on the cavity 8, a first hole 3a communicating with the cavity 8 is formed, and similarly, a second hole 3b communicating with the cavity 8 is formed in the silicon oxide film 9b on an opposite side to the first hole 3a.

Then, a sealing film 5 which seals each of the plurality of holes 3 is formed on an opening which opens in a front surface of the silicon oxide film 9b of each of the holes 3. Specifically, the opening of the first hole 3a which opens in the front surface of the silicon oxide film 9b is covered with a first sealing film 5a formed to seal the first hole 3a, and similarly, the opening of the second hole 3b which opens in the front surface of the silicon oxide film 9b is covered with a second sealing film 5b formed to seal the second hole 3b.

In the ultrasonic sensor 4 shown in FIGS. 1 and 2, the upper electrode 7 is formed into a hexagon in a plan view, and the cavity 8 corresponding to the upper electrode 7 is also formed into a hexagon in a plan view. As a result, the holes 3 each communicating with the cavity 8 are formed at locations close to the six corners of the hexagonal upper electrode 7, respectively. Accordingly, the plurality of sealing films 5, each of which seals each corresponding hole 3, are also formed at locations close to the six corners of the hexagonal upper electrode 7, respectively. By way of example, in a plan view, each of the holes 3 and each of the sealing films 5 sealing each hole 3 are provided on a diagonal line L of the hexagonal upper electrode 7. Thus, in each of the ultrasonic sensors 4, the plurality of holes 3 and the plurality of sealing films 5 can be disposed efficiently relative to the hexagonal upper electrode 7 and the hexagonal cavity 8.

In this case, the sealing film 5 such as the first sealing film 5a and the second sealing film 5b is a film deposited by a focused ion beam (FIB), which will be described later.

As described above, the plurality of ultrasonic sensors 4, which are the plurality of micro sensors, are formed on the semiconductor substrate 1. Each of the ultrasonic sensors 4 has the plurality of holes 3 and the plurality of sealing films 5 sealing the corresponding holes 3.

<Focused Ion Beam Device>

Figure 3:
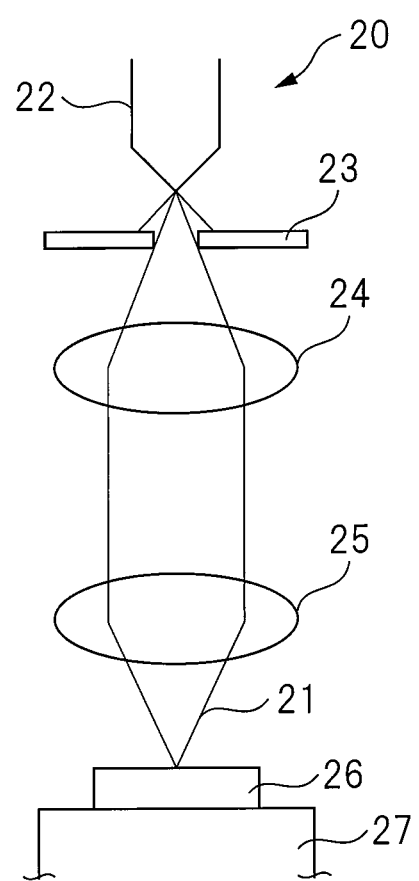
FIG. 3 is a schematic diagram of a focused ion beam device used in the first embodiment.

A schematic configuration of a focused ion beam device that emits a focused ion beam for forming the sealing film 5 of the first embodiment will then be described with reference to FIG. 3. FIG. 3 is a schematic diagram of the focused ion beam device used in the first embodiment to form the sealing film 5.

A focused ion beam device 20 shown FIG. 3 includes a vacuum chamber (not shown) in which a focused ion beam 21 is emitted onto a sample (a substrate such as the semiconductor substrate 1) 26. The vacuum chamber houses an ion source 22 that discharges gallium ions, an aperture 23 and a condenser lens 24 that condense an ion beam, an objective lens 25 that focuses the ion beam on a front surface of the sample 26, and a sample stage 27 holding the sample 26.

The ion beam which is condensed and focused on the front surface of the sample 26 is emitted onto the front surface of the sample 26 to process the sample 26.

<Matters Studied by Inventors of Present Application>

Figure 4:
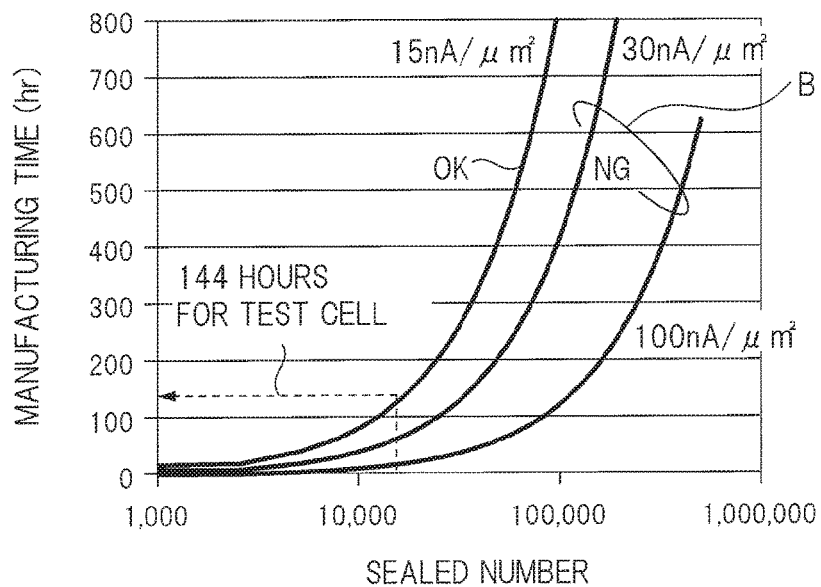
FIG. 4 is a graph indicating a relation between a sealed number and a manufacturing time, which has been studied by the inventors.
Figure 5:
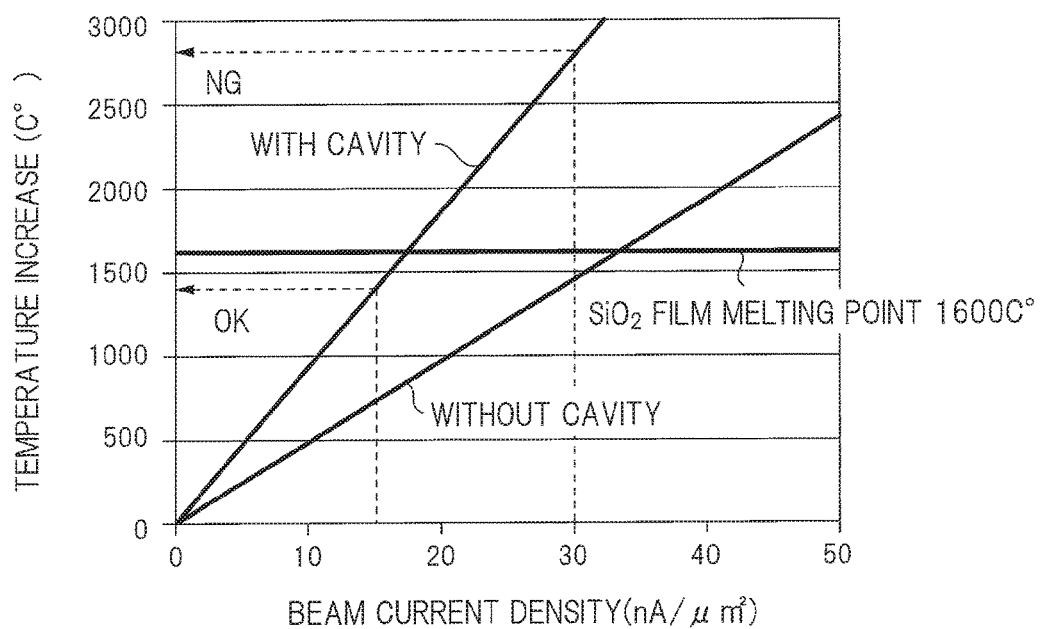
FIG. 5 is a graph indicating a relation between a beam current density and a temperature increase during a film-forming process, which has been studied by the inventors.
Figure 6:
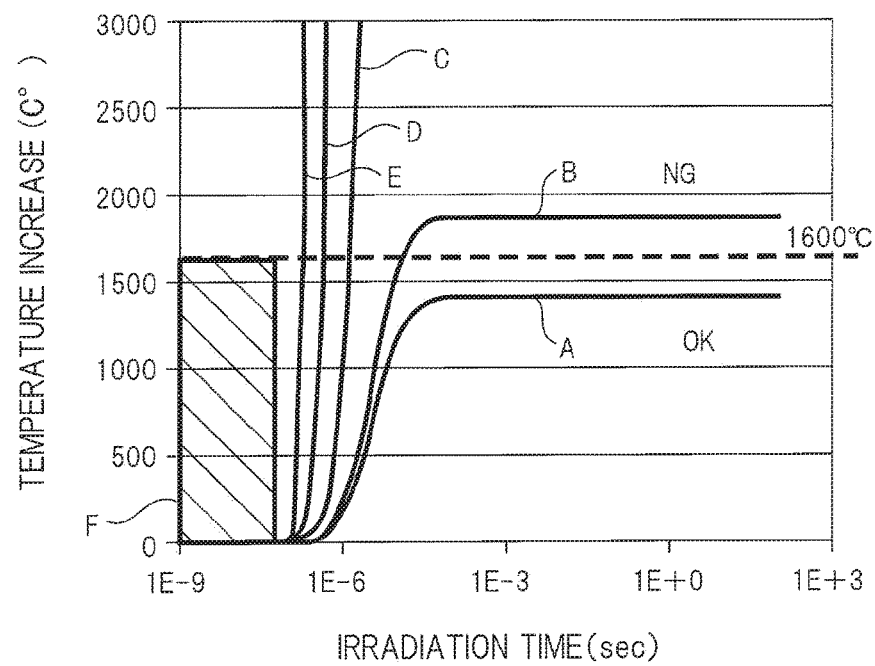
FIG. 6 is a graph indicating a relation between an ion beam irradiation time and a temperature increase, which has been studied by the inventors.

FIG. 4 is a graph indicating a relation between a sealed number and a manufacturing time, which has been studied by the inventors. FIG. 5 is a graph indicating a relation between a beam current density and a temperature increase during a film-forming process, which has been studied by the inventors. FIG. 6 is a graph indicating a relation between an ion beam irradiation time and a temperature increase, which has been studied by the inventors.

FIG. 4 is a graph indicating temperature increases during a film-forming process using focused ion beams having three types of beam current densities, in terms of the relation between the sealed number and the manufacturing time. Three types of beam current densities include, for example, 15 nA/$\mu$m$^2$, 30 nA/$\mu$m$^2$, and 100 nA/$\mu$m$^2$. The beam current density of 15 nA/$\mu$m$^2$ does not cause thermal structural destruction (a curve marked with OK in FIG. 4). The beam current densities of 30 nA/$\mu$m$^2$ and 100 nA/$\mu$m$^2$, however, cause thermal structural destruction (curves marked with NG in FIG. 4).

Note that, in the case of the ultrasonic sensor 4, a test cell has about 17,280 sealing spots, and one semiconductor chip has about 331,776 sealing spots, which means the number of sealing spots is significantly large. Under such circumstance, the curve representing the beam current density of 15 nA/$\mu$m$^2$ that does not cause thermal structural destruction (OK) defines a manufacturing time for 17,280 sealing spots of the test cell as 144 hours, which is a long manufacturing time to take.

Next, FIG. 5 is a graph indicating the relation between a beam current density and a temperature increase during the film-forming process for the case of the MEMS sensor having the cavity and the case of the MEMS sensor having no cavity. FIG. 5 indicates that, when the beam current density is 15 nA/$\mu$m$^2$, a temperature increase in each case of the MEMS sensor having the cavity and the MEMS sensor having no cavity is lower than 1600° C., which is the melting point of the silicon oxide film, and in both cases, thermal destruction of the MEMS sensors does not occur (OK).

When the beam current density is 30 nA/$\mu$m$^2$, however, the temperature increase of the MEMS sensor having no cavity does not reach 1600° C., while the temperature increase of the MEMS sensor having the cavity significantly exceed 1600° C., which is indicated as NG in the graph.

It is therefore understood from FIG. 5 that, in the MEMS sensor having the cavity, the cavity prevents heat conduction through the MESE sensor to slow down heat conduction, resulting in faster temperature increase and high temperature. In contrast, in the MEMS sensor having no cavity, heat conduction through the MEMS sensor is not prevented and performed faster, resulting in slow temperature increase and low temperature.

Next, FIG. 6 is a graph indicating the relation between an irradiation time and a temperature increase for each beam current density. In the case of the beam current density of 15 nA/$\mu$m$^2$ (curve A), the temperature increase saturates in a low-temperature range below 1600° C. In each case of the beam current density of 30 nA/$\mu$m$^2$ (curve B) and beam current densities of 100 nA/$\mu$m$^2$ (curve C), 1 $\mu$A/$\mu$m$^2$ (curve D), and 10 $\mu$A/$\mu$m$^2$ (curve E) which are larger than 30 nA/$\mu$m$^2$, however, a saturation temperature gets higher and higher.

In view of this, according to a manufacturing method of the MEMS sensor of the first embodiment, the focused ion beam 21 is emitted under a condition defined in a range F of FIG. 6 (hatched range where a temperature increase is low). Specifically, the range F where the temperature of the MEMS sensor does not reach 1600° C. by applying a beam having a large beam current density for a short time is used.

Figure 7:
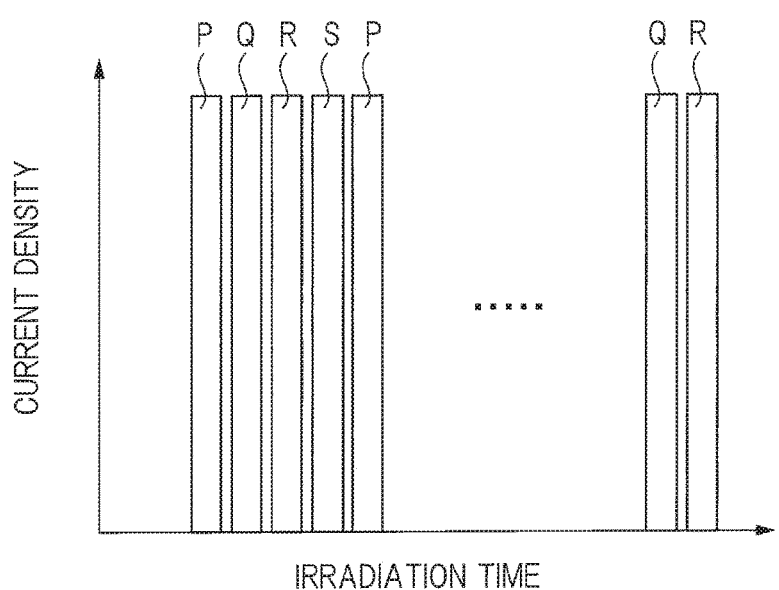
FIG. 7 is a graph indicating a relation between an ion beam irradiation time and a beam current density according to a manufacturing method of the MEMS sensor of the first embodiment.

A manufacturing method of the MEMS sensor of the first embodiment will then be described in detail. FIG. 7 is a graph indicating a relation between an ion beam irradiation time and a beam current density.

As shown in FIGS. 1 to 7, for example, the focused ion beam 21 is emitted onto sealing spots P and Q repeatedly to deposit thereon. In this process, the current density of the focused ion beam 21 is made larger, and the application time of the focused ion beam 21 is made shorter at each round of beam irradiation.

More specifically, the semiconductor substrate 1 is prepared first, the semiconductor substrate 1 including the first hole 3a and the second hole 3b that are formed in the silicon oxide film 9b such that they communicate with the cavity 8 formed between the lower electrode 6 and the upper electrode 7 on the semiconductor substrate 1 shown in FIG. 2. Subsequently, the focused ion beam device 20 shown in FIG. 3 irradiates the first hole 3a of the semiconductor substrate 1 with the focused ion beam 21 for a first predetermined time.

This process forms the first sealing film 5a, which seals the first hole 3a, on the first hole 3a. This is equivalent to the first sealing spot P shown in FIG. 7, for example.

Following the deposition on the first sealing spot P, the focused ion beam device 20 shown in FIG. 3 irradiates the second hole 3b shown in FIG. 2 with the focused ion beam 21 for a second predetermined time in the same manner.

This process forms the second sealing film 5b, which seals the second hole 3b, on the second hole 3b. This is equivalent to the deposition on the second sealing spot Q, which is performed after the deposition on the first sealing spot P shown in FIG. 7.

In these processes, each of the first predetermined time and the second predetermined time is the time in which thermal equilibrium of the silicon oxide film 9b can be maintained, that is, the ion beam irradiation time to such an extent that the silicon oxide film 9b is not destroyed by heat. Specifically, each of the first predetermined time and the second predetermined time is the irradiation time of the focused ion beam 21 that prevents the temperature of the silicon oxide film 9b upon irradiation with the focused ion beam from reaching 1600° C. (that keeps the temperature of the silicon oxide film 9b below 1600° C.), which is the melting point of the silicon oxide film 9b. In other words, film formation is performed in the range F shown in FIG. 6. For example, the current density of the focused ion beam 21 is 10 $\mu A/\mu m^2$, and the beam irradiation time, which is equivalent to each of the first predetermined time and the second predetermined time, is about 1E-8 (sec.) (E: exponential function).

Under such a condition, as shown in FIG. 7, sequential deposition on the sealing spots P, Q, R, S, P, . . . , Q, and R is repeated. As a result, the sealing film 5 is formed on each hole 3 shown in FIG. 2 at the sealing spots P, Q, R, S, etc., shown in FIG. 1.

Thus, according to the manufacturing method of the MEMS sensor of the first embodiment indicated in FIG. 7, an ion beam having a large beam current density is applied to a sealing spot for a short time, and this irradiation process is repeatedly performed in order on a plurality of sealing spots. In other words, high-rate deposition is performed using the range in which there is no temperature increase of the silicon oxide film 9b (range F in FIG. 6), for example.

As a result, in manufacture of the MEMS sensor (ultrasonic sensor 4), thermal destruction of the MEMS sensor can be prevented, while, at the same time, the TAT (Turn-Around Time) is shortened to allow the MEMS sensor to be manufactured efficiently.

A manufacturing method of the MEMS sensor according to modification examples of the first embodiment will then be described.

Figure 8:
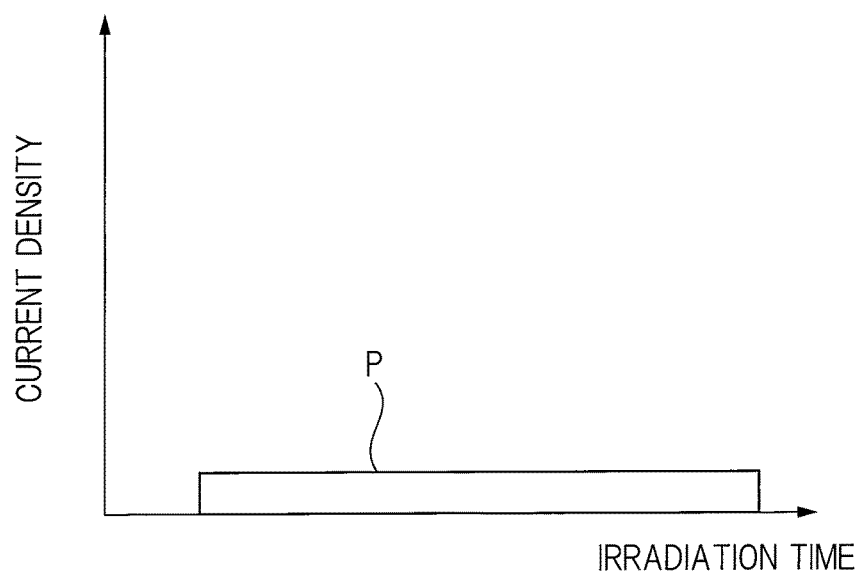
FIG. 8 is a graph indicating a relation between an ion beam irradiation time and a beam current density according to a first modification example of the manufacturing method of the MEMS sensor of the first embodiment.

FIG. 8 is a graph indicating a relation between an ion beam irradiation time and a beam current density according to a first modification example of the manufacturing method of the MEMS sensor of the first embodiment. This graph indicates the relation between the irradiation time and the current density of the focused ion beam 21 which forms one sealing film 5 sealing one hole 3.

In the first modification example, by irradiating each of the plurality of holes 3 formed in the silicon oxide film 9b in such a way as to communicate with the cavity 8 shown in FIG. 2 with the focused ion beam 21 having a predetermined beam current density shown in FIG. 3, the plurality of sealing films 5 respectively sealing the plurality of holes 3 are formed on the plurality of holes 3, respectively. At this time, according to the first modification example, the plurality of sealing films are formed simultaneously on the plurality of holes 3, respectively. That is, the plurality of sealing films 5 are formed all at once. FIG. 8 is the graph indicating the relation between the irradiation time and the current density of the focused ion beam 21 for forming one sealing film 5 (sealing spot P) in the case of simultaneously forming the plurality of sealing films 5. Accordingly, each of the plurality of holes 3 is irradiated simultaneously with the focused ion beam 21 at the current density and for the irradiation time indicated in FIG. 8.

Note that, to cause the focused ion beam device 20 to irradiate the plurality of holes 3 with the focused ion beam 21 simultaneously, a plurality of openings corresponding to the plurality of holes 3 are formed in a mask serving as the aperture 23 so as to allow the focused ion beam 21 to pass through each of the openings. Thus, the focused ion beam 21 can be simultaneously emitted onto the plurality of holes 3.

Also, the above predetermined beam current density set in the first modification example is the beam current density at which the thermal equilibrium of the silicon oxide film 9b can be maintained. That is, in the range shown in FIG. 6 where the temperature of the silicon oxide film 9b does not reach the melting point of 1600° C. (thermal equilibrium range, i.e., the range of beam current density in which the temperature of the silicon oxide film 9b is below 1600° C.), the focused ion beam 21 having a low current density (e.g., 15 $nA/\mu m^2$) is emitted simultaneously onto the plurality of holes 3 (continuously) for a long time, as indicated in FIG. 8 (parallel deposition).

According to the first modification example, irradiation with the ion beam having a low current density simultaneously forms the plurality of sealing films 5, and as a result, in the manufacture of the MEMS sensor (ultrasonic sensor 4), thermal destruction of the MEMS sensor can be prevented, and the TAT is shortened, so that the MEMS sensor can be manufactured efficiently.

Figure 9:
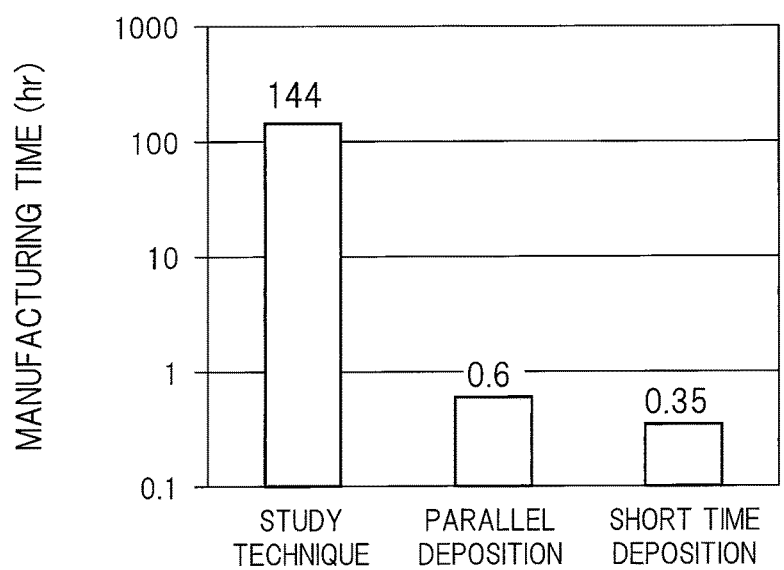
FIG. 9 is a graph indicating a manufacturing time taken by each manufacturing method of the MEMS sensor according to the first embodiment.

FIG. 9 is a graph indicating a manufacturing time taken by each manufacturing method of the MEMS sensor according to the first embodiment. That is, the graph indicates the results of comparison of the MEMS sensor manufacturing times taken by respective manufacturing methods.

In FIG. 9, "study technique" indicates a MEMS sensor manufacturing time in the case of forming the plurality of (predetermined number of) sealing films 5 by adopting the beam current density of 15 $nA/\mu m^2$ (curve A) indicated in FIG. 6. In this case, the manufacturing time is 144 hours.

"Short time deposition" in FIG. 9 is the case of adopting the method described with reference to FIG. 7, and in this method, an ion beam having a large beam current density is emitted onto a sealing spot for a short time and this irradiation process is repeatedly performed in order on a plurality of sealing spots to perform deposition. When the plurality of (predetermined number of) sealing films 5 are formed by this "short time deposition" method, the MEMS sensor manufacturing time is 0.35 hour, and the manufacturing time can be reduced to 1/411 of the manufacturing time taken by the "study technique." That is, adopting the "short time deposition" method reduces the TAT, so that the MEMS sensor can be manufactured efficiently.

Also, "parallel deposition" in FIG. 9 indicates the case of adopting the method described with reference to FIG. 8, and in this method, an ion beam having a low beam current density is emitted simultaneously onto a plurality of sealing spots continuously (for a long time) to form the plurality of sealing films 5 all at once. When the plurality of (predetermined number of) sealing films 5 are formed by this "parallel deposition" method, the MEMS sensor manufacturing time is 0.6 hour, and the manufacturing time can be reduced to 1/240 of the manufacturing time taken by the "study technique." That is, adopting the "parallel deposition" method also reduces the TAT, so that the MEMS sensor can be manufactured efficiently, as in the case of adopting the "short time deposition" method.

Note that the manufacturing time indicated by "parallel deposition" in FIG. 9 is the manufacturing time taken when, for example, about 240 sealing films 5 are formed in a 800 μm×800 μm area.

A second modification example of the first embodiment will then be described.

Figure 10:
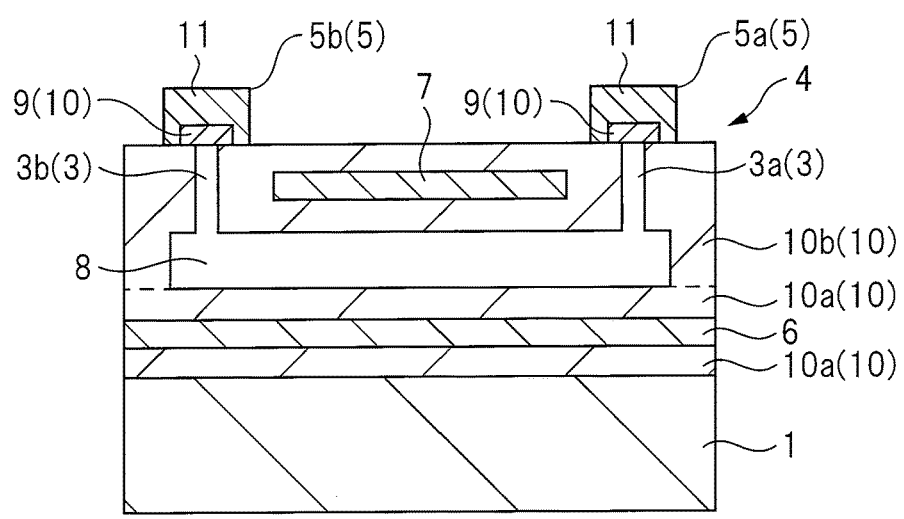
FIG. 10 is a cross-sectional view of a structure of a principle portion of a MEMS sensor according to a second modification example of the first embodiment.

FIG. 10 is a cross-sectional view of a structure of a principle portion of a MEMS sensor according to the second modification example of the first embodiment.

In the second modification example, as shown in FIG. 10, a silicon nitride film (SiN film) 10, which is denser than the silicon oxide film 9 shown in FIG. 2, is formed as an insulating film formed on the semiconductor substrate 1. Specifically, the MEMS sensor of the second modification example includes a silicon nitride film (an SiN film or the first layer) 10a formed on the semiconductor substrate 1, and a silicon nitride film (an SiN film or the second layer) 10b formed on the silicon nitride film 10a. The silicon nitride film 10a has the lower electrode 6 formed therein, and the silicon nitride film 10b has the upper electrode 7, the first hole 3a, and the second hole 3b formed therein.

Moreover, each of the first sealing film 5a and the second sealing film 5b formed on each hole 3, is a film containing a metal. In the structure shown in FIG. 10, each of the first sealing film 5a and the second sealing film 5b includes the silicon oxide film 9 or the silicon nitride film 10, and a metal film 11 covering the silicon oxide film 9 or the silicon nitride film 10. In other words, the hole 3 is sealed with the silicon oxide film 9 or the silicon nitride film 10, and the silicon oxide film 9 or the silicon nitride film 10 is covered with the metal film 11. Note that the metal film 11 is, for example, a tungsten film.

In this manner, the silicon nitride film 10 is adopted as the insulating film formed on the semiconductor substrate 1, and the sealing film 5 sealing the hole 3 is partially made of the metal film 11, so that penetration of moisture from outside can be prevented. As a result, reliability of the MEMS sensor (ultrasonic sensor 4) can be improved.

A third modification example of the first embodiment will then be described.

Figure 11:
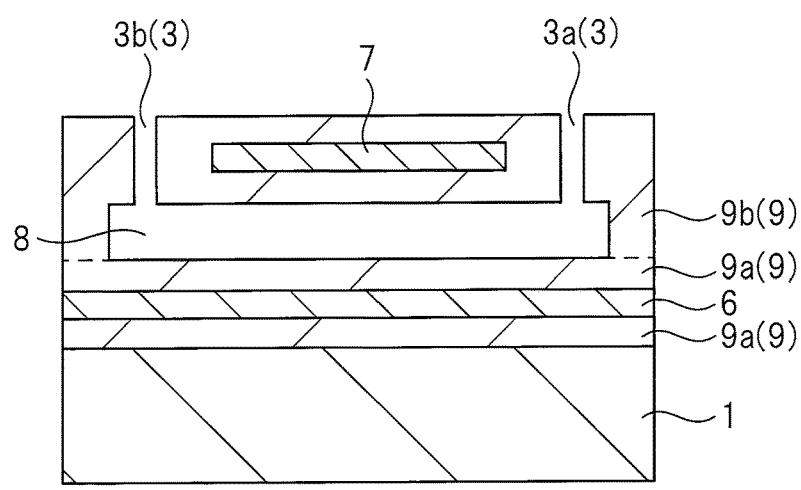
FIG. 11 is a cross-sectional view of a structure of a principle portion of a MEMS sensor according to a third modification example of the first embodiment before a sealing process.
Figure 12:
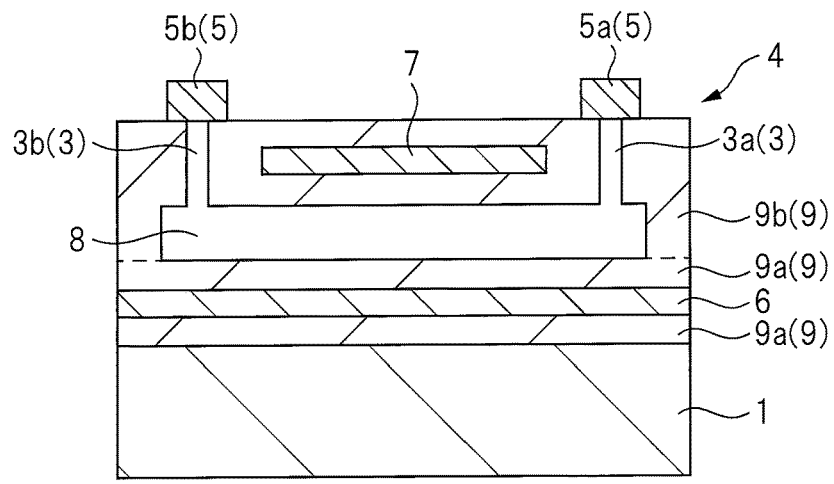
FIG. 12 is a cross-sectional view of the structure of the principle portion of the MEMS sensor according to the third modification example of the first embodiment after the sealing process.

FIG. 11 is a cross-sectional view of a structure of a principle portion of a MEMS sensor according to the third modification example of the first embodiment before the sealing process. FIG. 12 is a cross-sectional view of the structure of the principle portion of the MEMS sensor according to the third modification example of the first embodiment after the sealing process.

In the third modification example, by controlling a pressure in forming the sealing films 5 by the focused ion beam 21, an inner pressure of the cavity 8 is controlled when the cavity 8 is sealed up with the sealing films 5.

For example, in the structure before the sealing process shown in FIG. 11, the inner pressure of the chamber (not shown) of the focused ion beam device 20 shown in FIG. 3 is controlled by controlling a flow rate of a gas supplied into the chamber. By this process, a sealing pressure of the first sealing film 5a and the second sealing film 5b to be formed, shown in FIG. 12, is controlled. The above gas may be a gas used for film forming or may be an inert gas supplied into the chamber.

Specifically, the flow rate of the gas supplied into the chamber is controlled before the sealing process to control the inner pressure of the cavity 8 as well as an external pressure to the MEMS sensor, to 10 Pa, which is equal to a pressure at film formation. The sealing process is performed under this condition, that is, the first sealing film 5a and the second sealing film 5b are formed. Hence, the inner pressure of the cavity 8 can be controlled to 10 Pa.

Controlling the inner pressure of the cavity 8 in this manner improves a performance of the MEMS sensor. The inner pressure of the cavity 8 is, for example, related to a quality factor. For this reason, controlling the inner pressure of the cavity 8 is important to improve the performance of the MEMS sensor.

A fourth modification example of the first embodiment will then be described.

Figure 13:
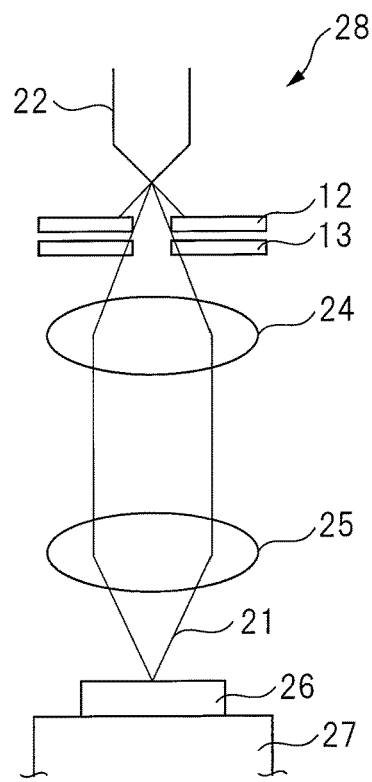
FIG. 13 is a schematic diagram of a structure of a focused ion beam device according to a fourth modification example of the first embodiment.
Figure 14:
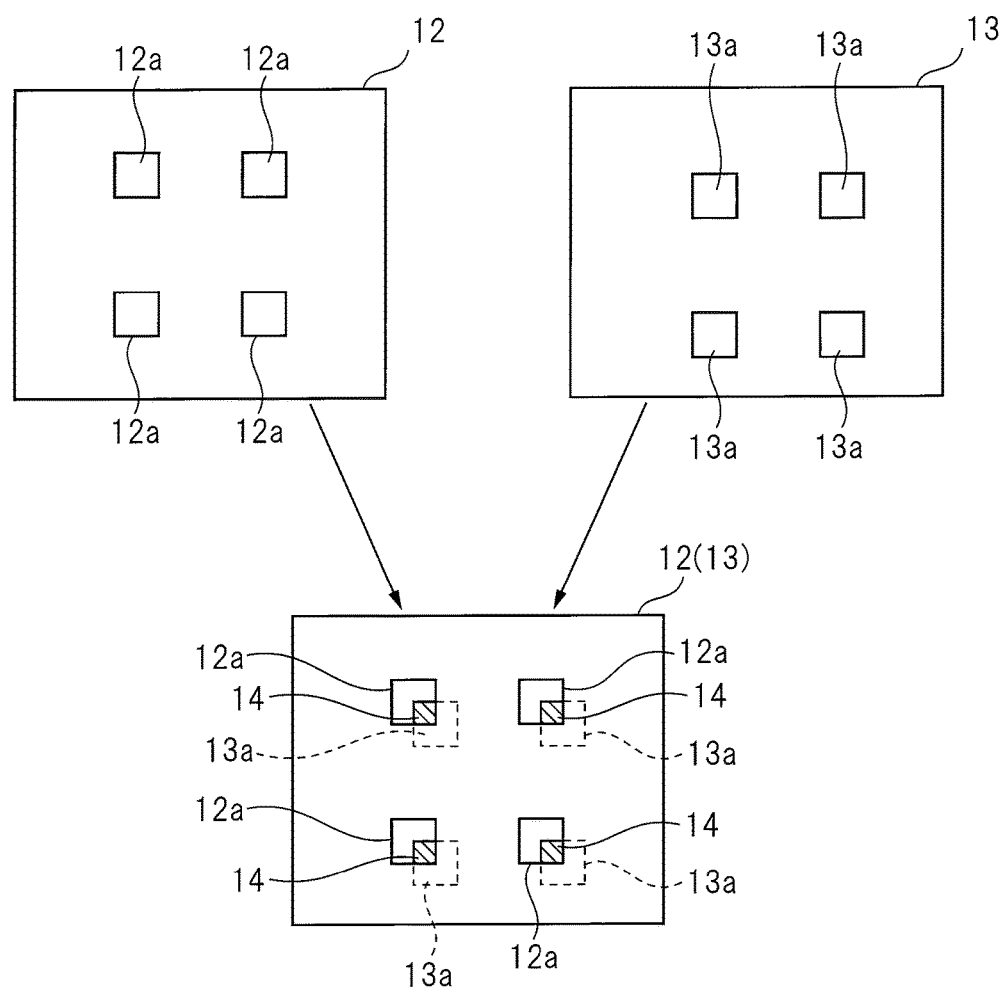
FIG. 14 is a plan view showing a method of using a projection mask in the focused ion beam device of FIG. 13.

FIG. 13 is a schematic diagram of a structure of a focused ion beam device according to the fourth modification example of the first embodiment. FIG. 14 is a plan view showing a method of using a projection mask in the focused ion beam device of FIG. 13.

In the fourth modification example, a focused ion beam device 28 shown in FIG. 13 includes a mask having a double-layer structure composed of a first mask and a second mask. Specifically, this focused ion beam device 28 is provided with a first projection mask (first mask) 12 and a second projection mask (second mask) 13 which are stacked one on top of another, in place of the aperture 23 shown in FIG. 3.

Note that, as shown in FIG. 14, the first projection mask 12 has a plurality of first openings 12a formed in such a way as to correspond to respective locations of the holes 3 to be formed, shown in FIG. 2, and the second projection mask 13 has a plurality of second openings 13a formed in the same manner as the first openings 12a. In this case, the first openings 12a and the second openings 13a are slightly shifted in position to each other.

When the focused ion beam 21 is emitted onto the sample 26, the plurality of first openings 12a of the first projection mask 12 are overlapped with the plurality of second openings 13a of the second projection mask 13 to form a plurality of third openings 14 (hatched portions), through which the ion beam passes to be condensed, as shown in FIG. 14. Overlapping the first openings 12a of the first projection mask 12 with the second openings 13a of the second projection mask 13 can form the third openings 14 each smaller in area than each of the first openings 12a and the second openings 13a.

Accordingly, causing the ion beam to pass through the third opening 14 can make a beam diameter of the focused ion beam 21 smaller.

Using the mask having the double-layer structure in which the first projection masks 12 and the second projection mask 13 are overlapped with each other in this manner improves a degree of freedom in changing a film-forming condition without increasing a type of mask.

A fifth modification example of the first embodiment will then be described.

Figure 15:
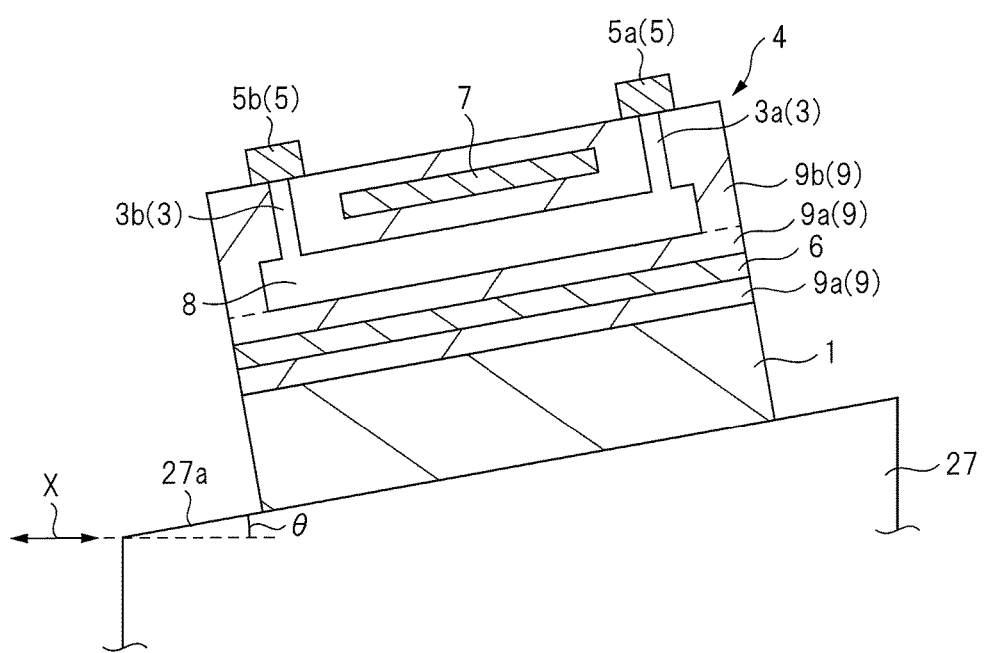
FIG. 15 is a schematic diagram of a structure of a sampling stage in a focused ion beam device according to a fifth modification example of the first embodiment.

FIG. 15 is a schematic diagram of a structure of a sampling stage in a focused ion beam device according to the fifth modification example of the first embodiment.

According to the fifth modification example, in the focused ion beam device 20 shown in FIG. 3, a substrate holding surface 27a of the sample stage 27 shown in FIG. 15 is tilted at an angle θ relative to a horizontal direction X. Specifically, the substrate holding surface 27a of the sample stage 27 which holds the sample 26 is formed such that the substrate holding surface 27a and the horizontal direction X make a predetermined angle θ (e.g., θ=15° or 30°).

With this structure, in the process of forming the plurality of sealing films 5 shown in FIG. 2, it is possible to irradiate the sample 26 (e.g., the semiconductor substrate 1) held on the sample stage 27 such that the sample 26 is tilted relative to the horizontal direction X at a predetermined angle, with the focused ion beam 21. Accordingly, when the plurality of sealing films 5 are formed, a pitch between the films can be made smaller than a pitch between the plurality of sealing films 5 formed on the horizontally held sample 26.

Note that, since the plurality of holes 3 shown in FIG. 2 are not always arranged at equal intervals, allowing for adjustment of the pitch between the sealing films 5 improves a degree of freedom in forming the plurality of sealing films 5.

Second Embodiment

Figure 16:
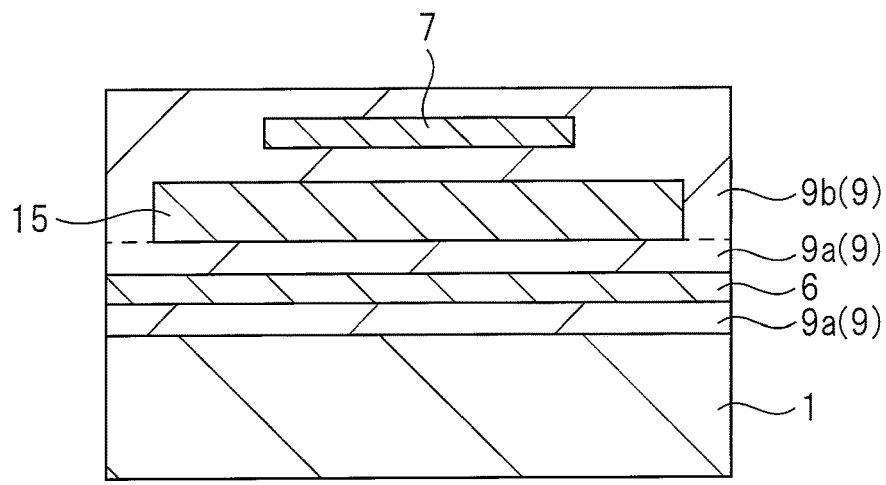
FIG. 16 is a cross-sectional view of a principle portion in a base forming process in a manufacturing method of a MEMS sensor according to a second embodiment of the present invention.
Figure 17:
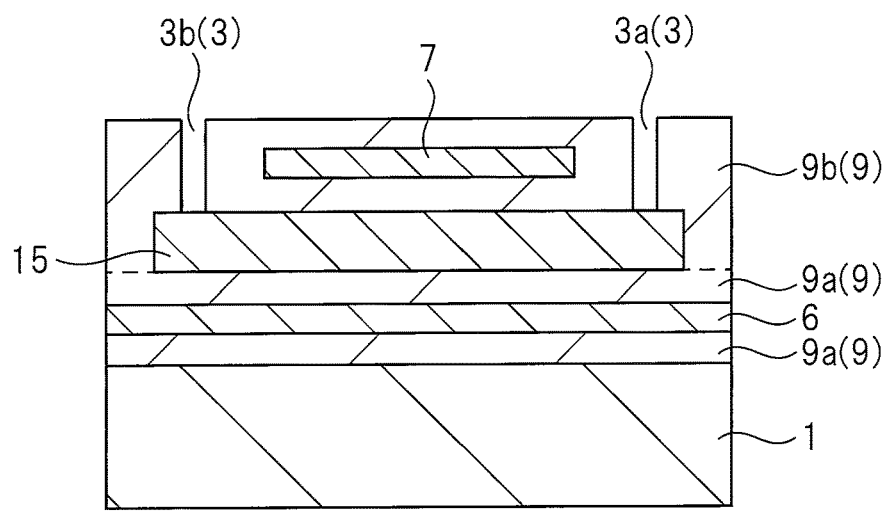
FIG. 17 is a cross-sectional view of a principle portion in a hole forming process in the manufacturing method of the MEMS sensor according to the second embodiment of the present invention.
Figure 18:
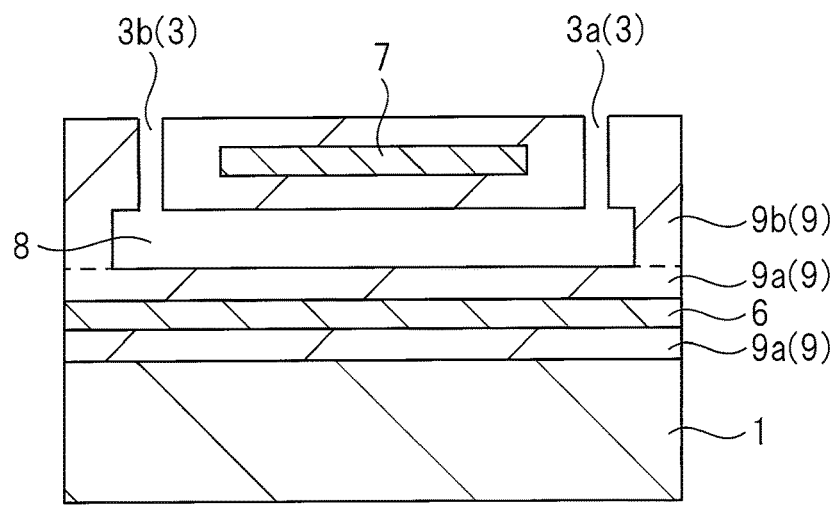
FIG. 18 is a cross-sectional view of a principle portion in a sacrifice layer removing process in the manufacturing method of the MEMS sensor according to the second embodiment of the present invention.
Figure 19:
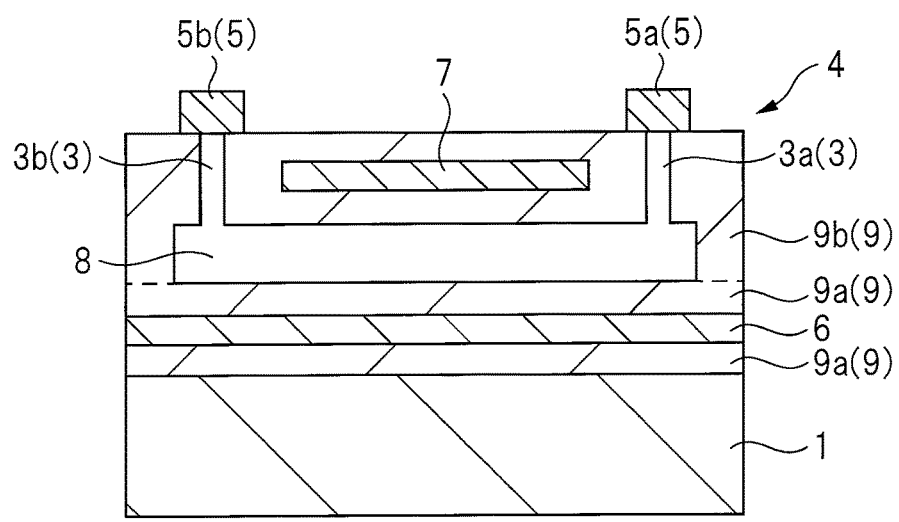
FIG. 19 is a cross-sectional view of a principle portion in a sealing process in the manufacturing method of the MEMS sensor according to the second embodiment of the present invention.

FIG. 16 is a cross-sectional view of a principle portion in a base forming process in a manufacturing method of a MEMS sensor according to a second embodiment of the present invention. FIG. 17 is a cross-sectional view of a principle portion in a hole forming process in the manufacturing method of the MEMS sensor according to the second embodiment of the present invention. FIG. 18 is a cross-sectional view of a principle portion in a sacrifice layer removing process in the manufacturing method of the MEMS sensor according to the second embodiment of the present invention. FIG. 19 is a cross-sectional view of a principle portion in a sealing process in the manufacturing method of the MEMS sensor according to the second embodiment of the present invention.

In the second embodiment, main processes including the base forming process to the sealing process according to the manufacturing method of the MEMS sensor will be described.

First, the base forming process shown in FIG. 16 will be described. On a semiconductor substrate 1, a silicon oxide film (a first layer) 9a, a silicon oxide film (a second layer) 9b on the silicon oxide film 9a, and a sacrifice layer 15 (a third layer) between the silicon oxide film 9a and the silicon oxide film 9b are formed. More specifically, the silicon oxide film (the first layer) 9a is formed as an insulating layer on the semiconductor substrate 1, and a lower electrode 6 is further formed on the silicon oxide film 9a. Subsequently, on the lower electrode 6, another silicon oxide film 9a is formed. Accordingly, a structure in which the lower electrode 6 is formed in the silicon oxide film 9a is provided. Then, the sacrifice layer 15 is further formed on an upper layer of the silicon oxide film 9a on the lower electrode 6.

Note that the sacrifice layer 15 (the third layer) is preferably a metal film made of, for example, titanium, tungsten, or molybdenum. Forming the sacrifice layer 15 with the metal film allows for highly precise formation of a cavity 8 (see FIG. 18) in a subsequent process where the cavity 8 is formed by removing the sacrifice layer 15.

Subsequently, the silicon oxide film (second layer) 9b serving as the insulating layer is formed on the sacrifice layer 15, and an upper electrode 7 is further formed on the silicon oxide film 9b. Another silicon oxide film 9b is then formed on the upper electrode 7. Accordingly, a structure in which the upper electrode 7 is formed in the silicon oxide film 9b is provided. Hence, the sacrifice layer 15 is formed between the lower electrode 6 and the upper electrode 7 via the insulating layer.

Subsequently, by irradiating a first hole formation spot of the silicon oxide film 9b with a focused ion beam 21 shown in FIG. 3 for a first predetermined time, a first hole 3a which reaches the sacrifice layer 15 is formed in the silicon oxide film 9b, as shown in FIG. 17. Also, by irradiating a second hole formation spot of the silicon oxide film 9b with a focused ion beam 21 for a second predetermined time, a second hole 3b which reaches the sacrifice layer 15 as well is formed in the silicon oxide film 9b.

Note that, when a plurality of holes 3 are formed by cutting processing with the focused ion beam 21 irradiated, the cutting processing can be performed in the same manner as the ion beam irradiation conditions shown in FIG. 7. That is, each of the first predetermined time and the second predetermined time is the time in which thermal equilibrium of the silicon oxide film (the second layer) 9b can be maintained, that is, the ion beam irradiation time to such an extent that the silicon oxide film 9b is not destroyed by heat. Specifically, the first predetermined time and the second predetermined time each represent the irradiation time of the focused ion beam 21 that prevents the temperature of the silicon oxide film 9b upon irradiation with the focused ion beam from increasing to 1600° C. (that keeps the temperature of the silicon oxide film 9b below 1600° C.), which is the melting point of the silicon oxide film 9b.

Under the above irradiation conditions of the focused ion beam 21, a step of forming the first hole 3a by the focused ion beam 21 and a step of forming the second hole 3b by the focused ion beam 21 are repeatedly performed in order.

Thus, by using the manufacturing method (ion beam irradiation conditions) indicated in FIG. 7, irradiation with an ion beam having a large beam current density is applied to each hole formation spot for a short time, and this irradiation is repeatedly applied to a plurality of hole formation spots in order to perform cutting processing of the holes.

Accordingly, in processing the plurality of holes in the manufacture of the MEMS sensor (ultrasonic sensor 4), thermal destruction of the MEMS sensor can be prevented, and the TAT (Turn-Around Time) is shortened, so that hole processing can be performed efficiently.

Note that, as the method of forming the plurality of holes 3 according to the second embodiment, a method may be adopted in which, by using the manufacturing method (ion beam irradiation conditions) indicated in FIG. 8, continuous irradiation with the focused ion beam 21 having a low current density for a long time is simultaneously applied to the plurality of hole formation spots to form the plurality of holes 3 all at once.

When this method is adopted for processing the plurality of holes in the manufacture of the MEMS sensor (ultrasonic sensor 4), thermal destruction of the MEMS sensor can also be prevented, and the TAT (Turn-Around Time) is shortened, so that the hole processing can be performed efficiently, as in the above case.

Note that formation of the plurality of holes 3 such as the first hole 3a and the second hole 3b may be performed not by cutting processing with the focused ion beam 21 but by dry etching in such a way that the silicon oxide film 9b is etched to form holes reaching the sacrifice layer 15.

Subsequently, after the plurality of holes 3 such as the first hole 3a and the second hole 3b are formed in such a way as to reach the sacrifice layer 15, the sacrifice layer 15 is removed through the first hole 3a and the second hole 3b to form the cavity 8, which communicates with the first hole 3a and the second hole 3b, between the silicon oxide film 9a and the silicon oxide film 9b.

In this process, for example, the sacrifice layer 15 is removed by wet etching through the first hole 3a and the second hole 3b to form the cavity 8.

Subsequently, as shown in FIG. 19, the sealing film 5 (the first sealing film 5a and the second sealing film 5b) sealing each hole 3 is formed on each of the first hole 3a and the second hole 3b.

Formation of the plurality of sealing films 5 according to the second embodiment is performed by using the irradiation conditions of the focused ion beam 21 indicated in FIG. 7, which has been described above in the first embodiment, and adopting the short time deposition method indicated in FIG. 9 or by using the irradiation conditions of the focused ion beam 21 indicated in FIG. 8 and adopting the parallel deposition method indicated in FIG. 9.

Note that the present invention is not limited to the above-described embodiment, and various modifications are included. For example, the above-described embodiment has been described in detail so that the present invention is easily understood, and is not limited to the one necessarily including all configurations described.

Also, a part of the configuration of an embodiment can be replaced with the configuration of other embodiments, and the configuration of other embodiments can be added to the configuration of an embodiment. In addition, other configurations can be added to, deleted from, or replaced with the part of the configuration of each embodiment. Note that each member described in the drawings and a relative size is simplified and idealized so that the present invention is easily understood, actual implantation is more complicated in shape.

Further, in the first embodiment and the second embodiment described above, description has been given of a case in which the substrate is the semiconductor substrate 1, byway of example. However, the substrate may be a glass substrate.

What is claimed is:

1. A manufacturing method of a MEMS sensor, comprising the steps of:
   (a) preparing a substrate on which a first layer and a second layer on the first layer via a cavity are formed and including a first hole and a second hole that are formed in the second layer in such a way as to communicate with the cavity;
   (b) after the step (a), by irradiating the first hole with a focused ion beam for a first predetermined time, forming a first sealing film that seals the first hole on the first hole; and
   (c) after the step (b), by irradiating the second hole with a focused ion beam for a second predetermined time, forming a second sealing film that seals the second hole on the second hole,
   wherein each of the first predetermined time and the second predetermined time is a time in which thermal equilibrium of the second layer is maintainable, and
   wherein the step (b) and the step (c) are performed repeatedly.

2. The manufacturing method of a MEMS sensor according to claim 1,
   wherein the MEMS sensor includes a plurality of first electrodes and a plurality of second electrodes that are disposed opposite to each other with a plurality of the cavities interposed therebetween in a film thickness direction.

3. The manufacturing method of a MEMS sensor according to claim 1,
   wherein each of the first predetermined time and the second predetermined time is an irradiation time of the focused ion beam that keeps a temperature of the second layer upon irradiation with the focused ion beam below a melting point of the second layer.

4. The manufacturing method of a MEMS sensor according to claim 1,
   wherein each of the first layer and the second layer is a silicon nitride film,
   wherein the first hole and the second hole are formed in the silicon nitride film serving as the second layer, and
   wherein each of the first sealing film and the second sealing film is a film containing a metal.

5. The manufacturing method of a MEMS sensor according to claim 1,
   wherein a flow rate of a gas supplied when the first sealing film and the second sealing film are formed is controlled to control a sealing pressure of the first sealing film and the second sealing film.

6. The manufacturing method of a MEMS sensor according to claim 1,
   wherein a focused ion beam device that emits the focused ion beam includes a mask having a double-layer structure composed of a first mask and a second mask, and
   wherein, at at least any of the step (b) or the step (c), when the focused ion beam is emitted, the focused ion beam is caused to pass through a third opening formed by overlapping a first opening of the first mask with a second opening of the second mask.

7. The manufacturing method of a MEMS sensor according to claim 1,
   wherein a focused ion beam device that emits the focused ion beam includes a sample stage holding the substrate, the sample stage having a substrate holding surface tilted relative to a horizontal direction, and
   wherein, at at least any of the step (b) or the step (c), the focused ion beam is emitted onto the substrate held on the sample stage such that the substrate is tilted relative to the horizontal direction.

8. A manufacturing method of a MEMS sensor, comprising the step of:
   on a substrate, forming a first layer and a second layer on the first layer via a cavity, and by irradiating each of a plurality of holes formed in the second layer in such a way as to communicate with the cavity with a focused ion beam having a predetermined beam current density, forming a plurality of sealing films each sealing each of the plurality of holes, on the plurality of holes, respectively,
   wherein the predetermined beam current density is a beam current density at which thermal equilibrium of the second layer is maintainable, and
   wherein the plurality of sealing films are formed simultaneously.

9. The manufacturing method of a MEMS sensor according to claim 8,
   wherein the MEMS sensor includes a plurality of first electrodes and a plurality of second electrodes that are disposed opposite to each other with a plurality of the cavities interposed therebetween in a film thickness direction.

10. The manufacturing method of a MEMS sensor according to claim 8,
    wherein the predetermined beam current density is a current density of the focused ion beam that keeps a temperature of the second layer upon irradiation with the focused ion beam below a melting point of the second layer.

11. The manufacturing method of a MEMS sensor according to claim 8,
    wherein each of the first layer and the second layer is a silicon nitride film,
    wherein the plurality of holes are formed in the silicon nitride film serving as the second layer, and wherein each of the plurality of sealing films is a film containing a metal.

12. The manufacturing method of a MEMS sensor according to claim 8,
wherein a flow rate of a gas supplied when the plurality of sealing films are formed is controlled to control a sealing pressure of the plurality of sealing films.

13. The manufacturing method of a MEMS sensor according to claim 8,
wherein a focused ion beam device that emits the focused ion beam includes a mask having a double-layer structure composed of a first mask and a second mask, and
wherein, upon irradiation with the focused ion beam at the step of forming the plurality of sealing films, the focused ion beam is caused to pass through a third opening formed by overlapping a first opening of the first mask with a second opening of the second mask.

14. The manufacturing method of a MEMS sensor according to claim 8,
wherein a focused ion beam device that emits the focused ion beam includes a sample stage holding the substrate, the sample stage having a substrate holding surface tilted relative to a horizontal direction, and
wherein, at the step of forming the plurality of sealing films, the focused ion beam is emitted onto the substrate held on the sample stage such that the substrate is tilted relative to the horizontal direction.

15. A manufacturing method of a MEMS sensor, comprising the steps of:
(a) on a substrate, forming a first layer, a second layer on the first layer, and a third layer between the first layer and the second layer;
(b) after the step (a), by irradiating a first hole formation spot of the second layer with a focused ion beam for a first predetermined time, forming a first hole in the second layer such that the first hole reaches the third layer;
(c) after the step (b), by irradiating a second hole formation spot of the second layer with a focused ion beam for a second predetermined time, forming a second hole in the second layer such that the second hole reaches the third layer;
(d) after the step (c), removing the third layer through the first hole and the second hole and then forming a cavity between the first layer and the second layer in such a way as to communicate with the first hole and the second hole; and
(e) after the step (d), forming a sealing film on each of the first hole and the second hole,
wherein each of the first predetermined time and the second predetermined time is a time in which thermal equilibrium of the second layer is maintainable, and
wherein, before the step (d), the step (b) and the step (c) are performed repeatedly.

* * * * *